United States Patent [19]
Koch et al.

[11] Patent Number: 6,146,858
[45] Date of Patent: Nov. 14, 2000

[54] METHOD FOR PRODUCING CELLULOSE DERIVATIVES

[75] Inventors: Rainhardt Koch; Frank Berendes, both of Köln, Germany; John Foster, Narara, Australia; Hans-Georg Rast, Bergisch Gladbach, Germany; Jürgen Engelhardt, Leverkusen, Germany; Jörg Neubauer, Walsrode, Germany; Wolfgang Koch, Bomlitz, Germany; Klaus Szablikowski, Walsrode, Germany

[73] Assignee: Wolff Walsrode AG, Walsrode, Germany

[21] Appl. No.: 09/462,046

[22] PCT Filed: Jun. 26, 1998

[86] PCT No.: PCT/EP98/03907

§ 371 Date: Feb. 14, 2000

§ 102(e) Date: Feb. 14, 2000

[87] PCT Pub. No.: WO99/02568

PCT Pub. Date: Jan. 21, 1999

[30] Foreign Application Priority Data

Jul. 9, 1997 [DE] Germany ............... 197 29 323

[51] Int. Cl.[7] .............. C12P 19/04; C12N 9/26; C12N 9/42; D06M 16/00; C08B 1/06

[52] U.S. Cl. ............ 435/101; 435/201; 435/209; 435/263

[58] Field of Search .................... 435/201, 101, 435/209, 263

[56] References Cited

U.S. PATENT DOCUMENTS

| | | | |
|---|---|---|---|
| 4,427,778 | 1/1984 | Zabriskie | 435/277 |
| 5,874,293 | 2/1999 | Miettinen-Oinonen et al. | 435/273 |
| 5,916,798 | 6/1999 | Lund et al. | 435/263 |
| 6,001,639 | 12/1999 | Schulein et al. | 435/263 |
| 6,071,735 | 6/2000 | Schulein et al. | 435/209 |

*Primary Examiner*—Herbert J. Lilling
*Attorney, Agent, or Firm*—Joseph C. Gil; Aron Preis

[57] ABSTRACT

Samples of commercial cellulose having high crystallinity (>80%) and a degree of polymerization of approximately 1500 were pretreated enzymatically under various conditions with commercial endoglucanases, before the chemical conversion to substituted cellulose derivatives was carried out. The enzymatically pretreated cellulose samples exhibited a significantly higher substitution, up to 222% higher, in comparison with control samples which had been treated with buffer without enzyme. The increase in substitution during the chemical reaction could be observed in the presence of various amounts of alkali, but fell as the amounts of alkali decreased. At the same degree of substitution of the cellulose derivative, the use of cellulose pretreated with endoglucanase significantly reduced the amount of alkali required by 60%, as compared with the use of cellulose pretreated only with buffer. Furthermore, by reducing the amount of water used in the reaction mixture in the chemical reaction, it was possible further to increase the substitution of enzymatically pretreated cellulose.

18 Claims, 4 Drawing Sheets

METHOD FOR PRODUCING CELLULOSE DERIVATIVES

The present invention relates to a process for the preparation of cellulose derivatives using cellulose pretreated with endoglucanases.

A reduction in the amount of alkali to be used by using cellulases in an enzymatic pretreatment stage has been described by Michels and Meister (DE 4 440 245 C1). Cellulases are enzyme complexes in which enzymes having different catalytic activities are combined: endoglucanases (EC 3.2.1.4), exoglucanases, which are also known as cellobiohydrolases (EC 3.2.1.74, EC 3.2.1.91) and β-glucosidases (EC 3.2.1.21). Those enzyme activities together decompose cellulose completely to glucose, whereas each on its own catalyses only partial steps of the decomposition. Endoglucanases, for example, cleave only endogenous β-1,4-glycosidic bonds in the amorphous regions of the polymer.

Surprisingly, endoglucanases can also be used alone in a similar pretreatment step for reducing the amount of alkali required. Moreover, the use of endoglucanases offers two important advantages in comparison with cellulases. Firstly, pretreatment with cellulases leads to a considerable loss of cellulose substrate to a marked reduction in the degree of polymerisation (DP value) and to a loss of cellulose substrate. Secondly, the cellulase activity is inhibited by soluble oligomeric decomposition products, which considerably restricts the possibility of the repeated use of a cellulase solution. That difference can be attributed to the different catalytic activities of the two enzymes.

Accordingly, the invention relates to a process by means of which cellulose of a suitable commercial quality is pretreated with endoglucanases prior to chemical conversion to commercial cellulose derivatives. With the aid of that pretreatment process, the degree of alkalisation of the cellulose and hence also the amount of chemicals used in the after-treatment steps can be reduced considerably. The process comprises treating the cellulose enzymatically with endoglucanases before it is introduced into the industrial manufacturing process. The cellulose pretreated in that manner and separated from the enzyme solution is hereinafter referred to as "activated". The cellulose derivatives prepared by the chemical conversion of activated cellulose are comparable with today's industrially manufactured products.

According to the invention, the process is as follows:
(A) A known weight of cellulose is pretreated with endoglucanase by incubation at a certain temperature and for a certain period of time in a suitable buffer system.
(B) The pretreated cellulose is then separated from the pretreatment mixture consisting of the buffer and the enzyme.
(C) The "activated" cellulose is then reacted chemically as under industrial conditions, but substantially less alkali is required for the reaction.

The conditions for the enzymatic pretreatment in step (A) can be varied as desired. Factors that affect the enzymatic pretreatment are:
(a) The origin of the endoglucanases, which originate from fungi, bacteria and plants, preferably from the fungi *Trichoderma reesei, Humicola insolens* and bacteria of the genera Bacillus, Cellulomonas, Sporocytophaga, Cytophaga, Clostridium. The use of Denimax Ultra L® (Novo Nordisk) is especially preferred.
(b) Buffer concentration from 1 to 1000 mM, preferred range from 10 to 100 mM, especially preferred range 50 mM sodium acetate or potassium phosphate according to the required buffer range. Other buffers or buffer/solvent mixtures are also in accordance with the invention.
(c) pH value of the buffer in the range from pH 1 to pH 13, preferred range from pH 4 to pH 10, especially preferred range from pH 5 to pH 7.5.
(d) Ratio of the weight of the cellulose to the volume of the buffer from 1 g:0.5 ml to 1 g:1000 ml, preferably from 1 g:5 ml to 1 g:100 ml, especially from 1 g:10 ml to 1 g:30 ml.
(e) Ratio of the weight of the enzyme to the weight of the cellulose from 0.01 to 50%, preferred range from 1 to 30%, especially preferred range from 3 to 12%.
(f) Incubation temperature from 0 to 100° C., preferred range from 20 to 80° C., especially preferred range from 50 to 60° C.
(g) Incubation time from a few minutes to several days, preferred range from 1 to 24 hours, especially preferred range from 2 to 3 hours.
(h) Shaking or stirring of the incubation mixture at from 1 to 10,000 rpm, preferred range from 10 to 2000 rpm, especially preferred range from 200 to 300 rpm.

The effect of those factors on the enzyme activity is known per se. Moreover, it has been shown that the cellulolytic enzymes obtained from various species have different degrees of affinity and activity. Changing those factors in the pretreatment process will, therefore, affect the activation of the cellulose. That in turn leads to changes in the degree of substitution of the chemically reacted cellulose derivatives.

The effects of the enzymatic pretreatment on the substitution values of chemically reacted cellulose can be demonstrated in two different ways. Firstly, the enzymatically pretreated cellulose has significantly higher values for the molecular substitution (MS) as compared with untreated controls. Secondly, the amount of alkali required for the chemical conversion reactions was significantly smaller when pretreated cellulose was used. The invention therefore has the advantage of reducing the amount of alkali required for the conversion process and nevertheless yielding the same end product. Moreover, the use of endoglucanases in the pretreatment stage offers two important advantages over cellulases:

The following interrelationships are shown in the Figures:

Pretreatment with Cellulase® led to a significant loss of material, which could be recognised by a reduction in weight and the fall in the DP value. The endoglucanases studied, on the other hand, exhibited only a negligible loss of cellulose (FIGS. 1 and 3). The loss of material was due to the decomposition of the cellulose to soluble monomeric and oligomeric products in step (A), a loss of very fine particles in the separation in step (B) and a loss of material on transfer to the chemical reaction vessels in (B/C). After 20 hours' incubation at a temperature of 36° C. and a buffer pH of 5, the cellulose studied exhibited a gradual loss of material of up to 19% of the initial weight, depending on the enzyme concentration.

By contrast, the endoglucanases caused a negligible weight loss (FIG. 1). Incubation of cellulose with a Cellulase® concentration of 2% (w/w enzyme weight to cellulose weight) under optimum conditions, that is to say pH 5.5 and 50° C., likewise resulted in a gradual loss of material of approximately 6% after an incubation period of 180 minutes. Cellulose samples with a concentration of 6% and 15% (v/w—enzyme volume to cellulose weight) of the endoglucanase Denimax Ultra L® exhibited a negligible loss of material after the same incubation time at the optimum pH of 7 and a temperature of 60° C. A concentration of 6%

Cellusoft Ultra L® resulted in a negligible loss of material after 90 minutes at pH 5.5 and 50° C.; thereafter there was an almost exponential loss of cellulose material to approximately 5% after 180 minutes (FIG. 3).

The cellulase activity is inhibited by the soluble oligomeric decomposition products. Consequently, the use of the buffer/cellulase mixture after separation of the pretreated cellulose in step (B) is limited. The absence of dissolved decomposition products and their inhibiting effect on the endoglucanases means that the buffer/endoglucanase mixture can readily be used again for pretreating further cellulose samples, as a result of which material costs are reduced. As well as demonstrating the decomposition activity of the enzymes used in the Examples below, the curves are also important for calculating standardised pretreated sample weights. After pretreatment, the same equivalent dry weights of cellulose material were thus present for each sample and were exposed to the same chemical conversion conditions.

FIG. 2 shows the changes in the degree of polymerisation (DP) for cellulose samples pretreated with different concentrations of cellulase and endoglucanases in accordance with the description relating to FIG. 1. The degree of polymerisation fell as the enzyme concentration increased, so that maximum differences of approximately 13% and 15% were determined for samples pretreated with Denimax Ultra L® and Cellulase® . The Cellusoft Ultra L® samples exhibited a slightly higher endo-activity with a 20% reduction as compared with the samples without enzymatic pretreatment. A similar trend was observed for the samples pretreated under optimum conditions (FIG. 4). In those cases, the reduction in the degree of polymerisation, less than 10% in each case, was not lower.

Enzymatic pretreatment of the cellulose had a marked effect on the degree of substitution of the cellulose derivatives which were etherified by propylene oxide in an alkaline medium to form hydroxypropylcellulose (HPC) (FIG. 5). During incubation only in buffer (enzyme content=0%), degrees of substitution of from 0.4 to 0.5 mol % were achieved. The endoglucanases (Denimax Ultra L® and Cellusoft Ultra L®) exhibited the same effectiveness as the cellulase. The change in the substitution in dependence on the enzyme concentration was characterised in all tested enzymes by the occurrence of optima.

FIG. 6 shows the effects of alkali on the substitution values of the cellulose derivatives after the chemical reaction. Increasing amounts of NaOH gave maximum MS values of 1.1 mol % in cellulose pretreated only with buffer. By pretreatment with the endoglucanase Denimax Ultra L, MS values of up to 2 mol % could be achieved. The effect of the enzymatic activation appeared most clearly after a chemical reaction in the presence of from 1.2 to 1.6 g of NaOH per g of cellulose. Denimax Ultra L was used in an amount of 15% v/w and the reaction was carried out at 200 rpm. Under those conditions, approximately 28% less NaOH was required to prepare HPC having a degree of substitution of 1.0 after enzymatic pretreatment.

In the samples containing enzymatically pretreated cellulose as substrate, the degree of substitution can be increased still further by reducing the water content in the reaction mixture. Cellulose samples were pretreated by incubation for a period of 2 hours at 60° C., with vigorous shaking (200 rpm), in water, buffer and buffer containing enzyme (FIG. 7). After the incubation, the samples were filtered under slight pressure. The water retention values for the cellulose samples varied according to the filtration time and pressure. However, the relative water retention values between the various treatment methods remained the same. This shows that under the test conditions chosen here, although the enzymatic pretreatment changes the cellulose structure, it does not bring about any significant change in the water retention capability. However, the chemical conversion of those samples so pretreated exhibited marked differences in the degree of molar substitution of their derivatives. The derivatives prepared from enzymatically pretreated cellulose exhibited degrees of substitution which were up to 91% higher as compared with cellulose samples which had not been treated enzymatically. That increase could be raised significantly to 161% by optimising the water content in the reaction mixture.

FIG. 7 also shows the effect of the water involved in the reaction on the synthesis of the derivatives. In the case of cellulose samples pretreated by incubation in water, the synthesised derivatives had a maximum molecular substitution of 0.8 with a water content of 3.1 g per 1 g of cellulose. Samples pretreated with buffer possessed a similar water content optimum with a slightly higher molecular substitution of approximately 0.88. As the water content fell, the samples pretreated with buffer exhibited increasingly higher MS values than samples treated with water. In contrast, derivatives synthesised from enzymatically pretreated samples exhibited higher MS values at all the water contents studied, with a maximum MS value of 2.35 at 1.45 g of water per 1 g of cellulose. Therefore, the enzymatically pretreated cellulose samples used as substrates for the chemical conversion required approximately 47% less water in order to achieve, as compared with samples which had not been treated enzymatically, a maximum MS value higher by 161%.

and 15% (v/w) (O) Denimax Ultra L® in 50 mM potassium phosphate buffer having a pH value of 7.0. The samples were removed at regular intervals and their wet and dry weights were determined in accordance with FIG. 1. The losses of material were given as a percentage of the initial weights.

Figure 3:
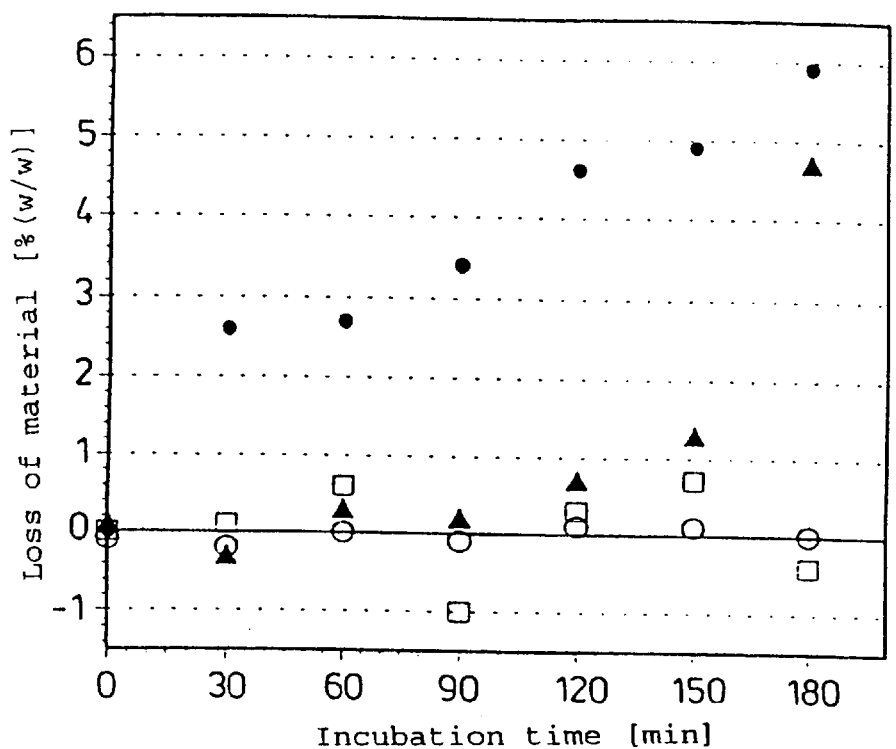
FIG. 3 Change in the loss of cellulose material with time. Cellulase® (●), Denimax Ultra L® (□ and O) and Cellusoft Ultra L® (▽). 1.5 g samples of cotton cellulose from Wolff Walsrode were shaken (200 rpm) at 50° C. and incubated with 2% (w/w, enzyme weight to cellulose weight) Cellulase® in 50 mM sodium acetate buffer having a pH value of 5.5. 1.5 g cellulose samples were incubated under the same conditions with 6% (v/w, enzyme volume to cellulose weight) Cellusoft Ultra L®. Further 1.5 g cellulose samples were shaken (200 rpm) at 60° C. and incubated with 6% (□)
Figure 4:
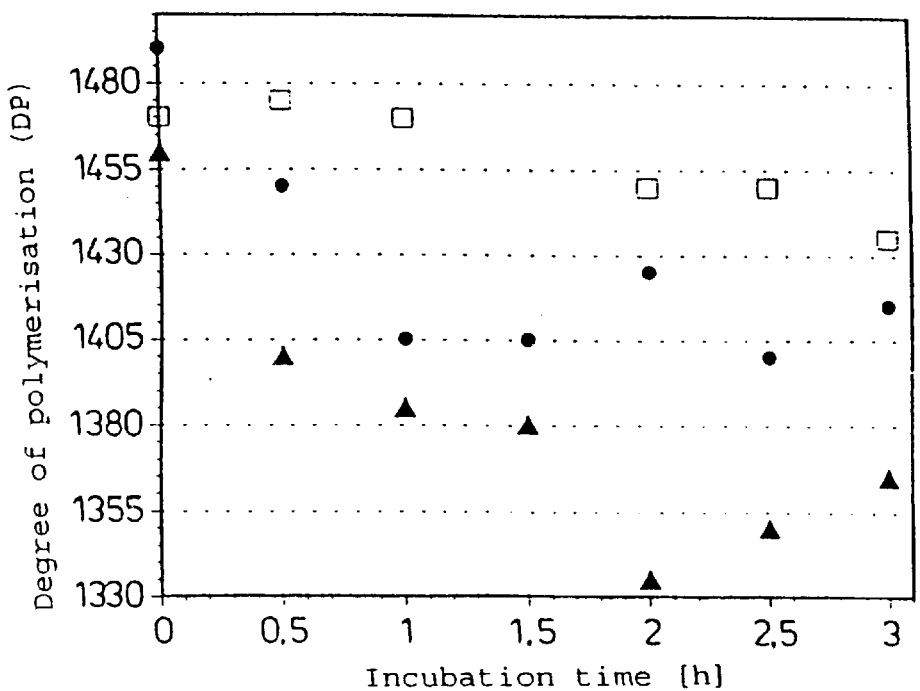

FIG. 4 Change in the degree of polymerisation of the cellulose with time. Cellulose samples were decomposed in the presence of various concentrations of the enzymes Cellulase® (●), Denimax Ultra L® (□) and Cellusoft Ultra L® (▽) according to FIG. 3; the samples were analysed and their respective degrees of polymerisation were determined.

Figure 5:
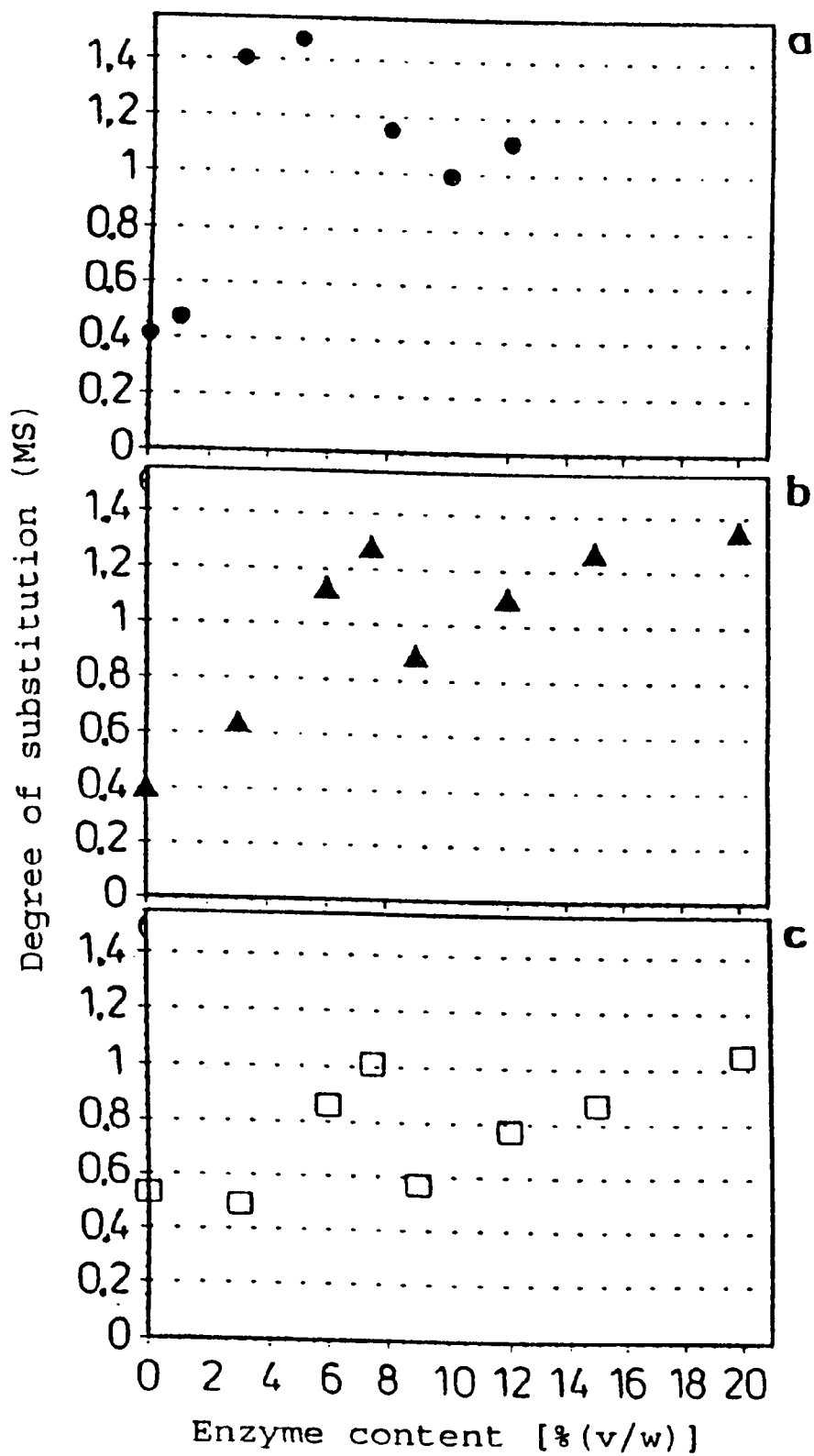

FIG. 5 Change in the degree of substitution of enzymatically pretreated cellulose derivatives in dependence on the enzyme concentration. Prior to the chemical conversion, the cellulose samples were pretreated with buffer and various enzyme concentrations. Enzyme pretreatment of the samples with (a) Cellulase® (●), (b) Cellusoft Ultra L® (▽) and (c) Denimax Ultra L® (□) was carried out in accordance with the description relating to FIG. 1. Pretreated cellulose samples each having a weight of 5 g and having water retention values of 2 g/g were then reacted chemically by incubation at 80° C., with shaking at 50 rpm, for 3 hours in the presence of 50 ml of a mixture of dioxane and water (9:1) at a molar ratio of cellulose to propylene oxide of 1:5 and a molar ratio of cellulose to 50% sodium hydroxide of 1:1.5. The degree of substitution of the product was determined by means of solid-state NMR.

Figure 2:
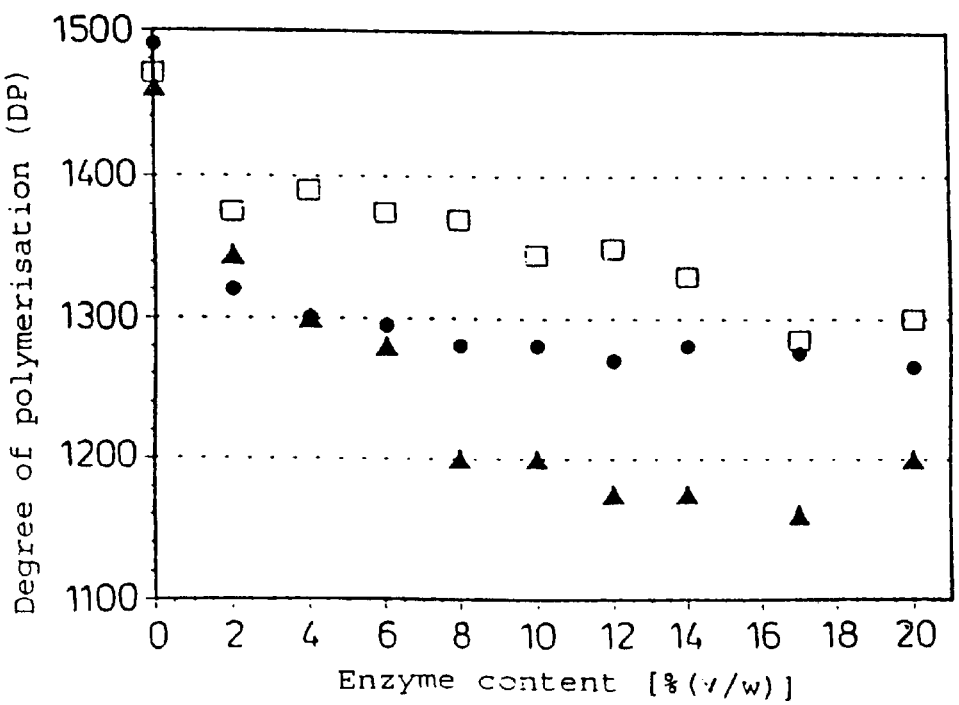
FIG. 2 Change in the degree of polymerisation of the cellulose under the action of commercial cellulolytic enzymes. Cellulose samples were decomposed in the presence of various concentrations of the enzymes Cellulase® (●), Denimax Ultra L® (□) and Cellusoft Ultra L® (▽) according to FIG. 1; the samples were analysed and their respective degrees of polymerisation were determined.
Figure 6:
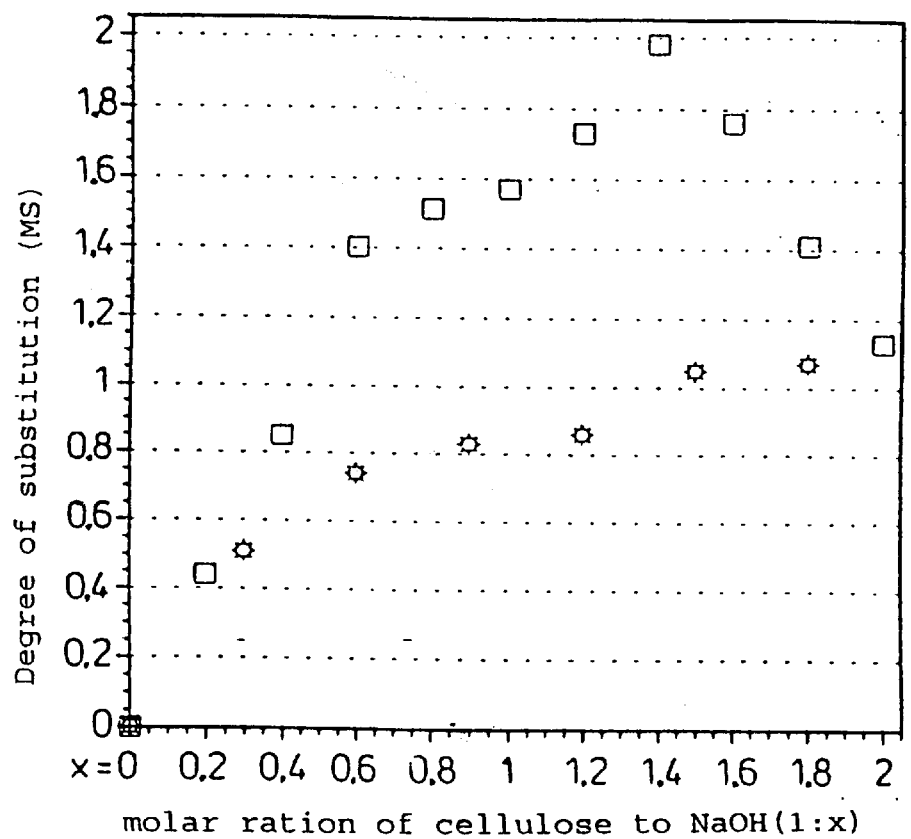

FIG. 6 Change in the degree of substitution of enzymatically pretreated cellulose derivatives in dependence on the alkali concentration. Cellulose samples were pretreated with potassium phosphate buffer (✪) or with a concentration of 15% (v/w) Denimax Ultra L® (□) in accordance with the description relating to FIG. 2. The pretreated samples each having a weight of 5 g and having water retention values of 2 g/g were reacted chemically in accordance with the description relating to FIG. 5, except that shaking was carried out at 200 rpm before and during the chemical conversion.

Figure 7:
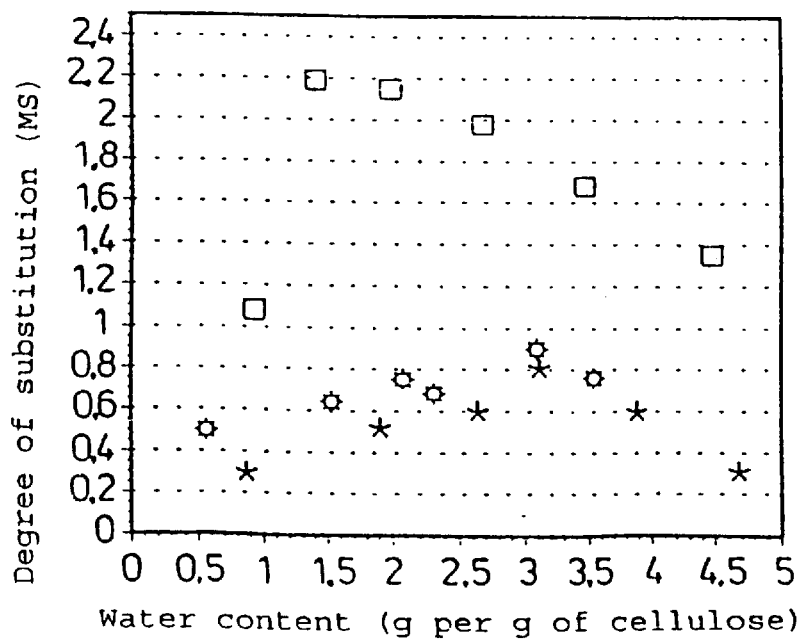

FIG. 7 Maximising the substitution of enzymatically pretreated cellulose derivatives by optimising the water content. Cellulose pretreated by pre-soaking in water (*), cellulose pretreated with buffer (✪) and cellulose pretreated with Denimax Ultra L® (□) from Novo Nordisk. 5 g samples of Temming 500 linters were shaken (200 rpm) at 60° C. and incubated for 2 hours in potassium phosphate buffer (50 mM, pH 7) with and without 6% (v/w—enzyme volume to cellulose weight) Denimax Ultra L® endoglucanase. Samples pretreated with water were incubated under the same conditions in only water. After the incubation, the cellulose samples were separated from the mixture and subjected to the chemical conversion in accordance with the description relating to FIG. 5.

EXAMPLES

Example 1
Enzymatic Pretreatment—Change in the Enzyme Concentration

Figure 1:
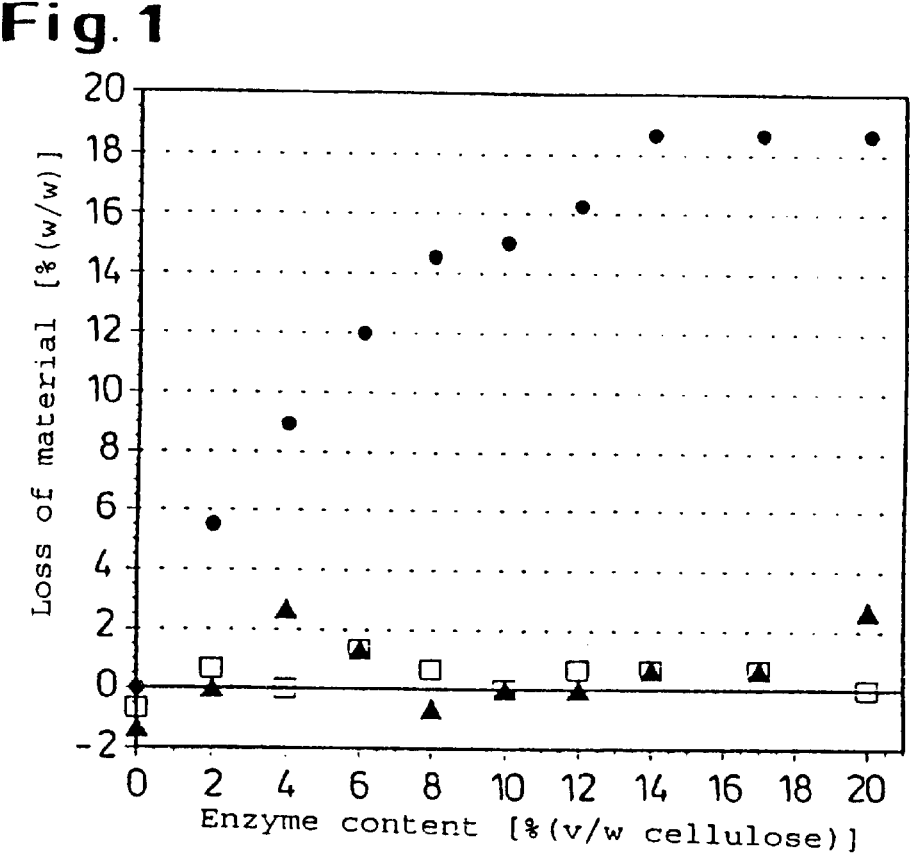
FIG. 1 Loss of cellulose material under the action of commercial cellulolytic enzymes. Cellulase® from Merck (●), endoglucanases—Denimax Ultra L® (□) and Cellusoft Ultra L® (▽) from Novo Nordisk. 1.5 g samples of Temming T 500 linters were shaken (200 rpm) at 36° C. and incubated for 20 hours with various enzyme concentrations. The Cellulase® and Cellusoft Ultra L® samples were incubated in 50 mM sodium acetate buffer having a pH value of 5, and the Denimax Ultra L® samples were incubated in 50 mM potassium phosphate buffer having a pH value of 7.1. After the incubation, the samples were cooled in an ice bath, filtered and washed under slight pressure. The wet weights of the pretreated cellulose material were measured and the samples were dried in a vacuum oven at 65° C. for 24 hours. Before the dry weights were determined, the samples were cooled to room temperature. The losses of material were given as a percentage of the initial weights.

The decomposition curves shown in FIG. 1 were used to calculate the initial weights of cellulose required to prepare 5 g of pretreated activated cellulose substrate. Samples of commercial cotton cellulose having high crystallinity (>80%) and a degree of polymerisation of approximately 1500 were incubated at 36° C. with vigorous shaking (200 rpm) for 20 hours in a suitable buffer in a ratio of cellulose to buffer of 1 g to 15 ml in the presence of various enzyme concentrations. The samples were incubated in 50 mM sodium acetate buffer at pH 5 with Cellusoft Ultra L® concentrations of from 0 to 15% (v/w). Samples containing the same concentrations of Denimax Ultra L® were incubated in 50 mM potassium phosphate buffer at pH 7.1. After the incubation, the samples were cooled in an ice bath, filtered and washed under slight pressure using a no. 4 Buchner funnel. The pretreated samples having equivalent dry weights of 5 g and water retention values of 2 g/g of cellulose were then transferred to glass reaction vessels and subjected to the chemical conversion process described in Example 2 below. All stages of the pretreatment process were subjected to gravimetric analysis and exhibited complete transformation of the material into the chemical conversion stage.

Example 2
Preparation of Hydroxypropylcellulose (HPC)

50 ml of a solution of dioxane and water (9:1) were added to the cellulose samples from Example 1 pretreated with endoglucanase. 50% sodium hydroxide and 100% propylene oxide were added to those mixtures in molar ratios of cellulose to substance of 1:1.5 and 1:5, respectively, and the contents were mixed by gentle slewing.

The samples were then reacted under pressure by reaction at 80° C. for a period of 3 hours with gentle shaking (50 rpm). The reacted samples were removed and left to cool for 5 minutes. The catalytic alkali was neutralised by addition of 100% acetic acid in a molar ratio of 1:1. The volatile contents were removed by placing the reaction vessels in a slight air stream in a fume cupboard for 15 hours. The HPC was then purified by vigorous mixing with 200 ml of distilled water and dialysis (MWCO 1000) of the mixture for 5 hours under flowing distilled water and then for 15 hours in a 2.5 liter water bath of distilled water at 4° C. The samples purified by dialysis were then dried in evaporating dishes under dust-free conditions at 70° C. in a continuous low-pressure stream. The dried HPC samples were then comminuted by grinding at low temperatures and analysed by means of solid-state NMR. All stages of the process were subjected to gravimetric analysis and exhibited complete transformation of the material into the respective subsequent process stage. The NMR results were used quantitatively to calculate the molecular substitution (MS) and qualitatively to confirm the purity of the HPC. The results are shown in FIG. 5 and summarised below.

| Sample | Opt. Conc. (%) | Loss of material (%) | DP | DP (%) | MS | MS (%) |
|---|---|---|---|---|---|---|
| Sodium acetate buffer, pH 5 | — | 0 | 1475 | 100 | 0.41 | 100 |
| Potassium phosphate buffer, pH 7 | — | 0 | 1470 | 100 | 0.50 | 100 |
| Cellulase ® | 4.0 | 9 | 1300 | 88.1 | 1.50 | 366 |
| Endoglucanase - Cellusoft Ultra L ® | 6.6 | 0 | 1220 | 82.7 | 1.32 | 322 |
| Endoglucanase - Denimax Ultra L ® | 7.0 | 0 | 1360 | 92.5 | 1.05 | 201 |

Comparison Examples

For Examples 1 and 2, controls pretreated only with buffer and without enzyme were used. In addition, a commercially available cellulase from Merck was also tested in a comparison. In that case, the cellulose samples were pretreated by incubation at 36° C. and 200 rpm for 20 hours in 50 mM sodium acetate buffer (pH 5) containing Cellulase® concentrations of from 0 to 15% (w/w).

Example 3
Enzymatic Pretreatment—Optimum Conditions

The decomposition curves shown in FIG. 3 were used to calculate the initial weights required to prepare pretreated activated cellulose samples having equivalent dry weights of 5 g. Samples of commercial cotton cellulose having high crystallinity (>80%) and a degree of polymerisation of approximately 1500 were incubated at 50° C. with vigorous shaking (200 rpm) for 2 hours in 50 mM sodium acetate buffer at pH 5.5 with a ratio of cellulose to buffer of 1 g to 15 ml in the presence of a concentration of 6% (v/w) Cellusoft Ultra L®. Samples containing concentrations of 6% and 15% (v/w) Denimax Ultra L® were incubated at 60° C. and 200 rpm for 2 hours in 50 mM potassium phosphate buffer at pH 7.0. After the incubation, the samples were cooled in an ice bath, filtered and washed under slight pressure using a no. 4 Buchner funnel. The pretreated samples having equivalent dry weights of 5 g and water retention values of approximately 2 g/g were then subjected to the chemical conversion process described in Examples 4 and 5 below. All stages of the pretreatment process were subjected to gravimetric analysis and exhibited complete transformation of the material into the chemical conversion stage.

Example 4
Preparation of Hydroxypropylcellulose (HPC)

The cellulose from Example 3 pretreated with 6% (v/w) Denimax Ultra L® was subjected to the chemical conversion process described in Example 2, but with an important exception: 50% sodium hydroxide was added in variable molar ratios of cellulose to alkali of from 1:0 to 1:2.0. The HPC was then purified according to Example 2 and analysed by means of NMR. The results are shown in FIG. 6.

Example 5
Preparation of Hydroxypropylcellulose (HPC)

The cellulose from Example 3 pretreated with 15% (v/w) Denimax Ultra L® was subjected to the chemical conversion process described in Example 4, but with an important exception: the shaking speed during the chemical conversion was raised to 200 rpm. The HPC was then purified according to Example 2 and analysed by means of NMR. The results are shown in FIG. 7.

For Examples 3, 4 and 5, controls pretreated only with buffer and without enzyme were used. In addition, a molar ratio of cellulose to sodium hydroxide of 1:0 in the chemical conversion yielded controls for the required amount of catalytic alkali.

Example 6

5 g samples of commercial cotton cellulose (>80%, degree of polymerisation 1600) from Wolff Walsrode were incubated at 60° C. with increased shaking (200 rpm) for 2 hours in buffer (pH 7, 50 mM) and in buffer containing 15% (v/w—enzyme volume to cellulose weight) of the endoglucanase Denimax Ultra L® (Novo Nordisk). After the incubation, the cellulose samples were cooled in an ice bath and filtered under slight pressure. The wet weights of the samples were then measured and the water retention values were calculated.

The samples were then reacted to hydroxypropylcellulose (HPC) by reaction at 80° C. for 3 hours with shaking at 200 rpm in the presence of 30 ml of a mixture of dioxane and water (9:1) together with propylene oxide and sodium hydroxide (50%) in molar ratios of cellulose to reactant of 1:5 and 1:1.5. After the reaction and subsequent cooling, the samples were neutralised by mixing with acetic acid (100%) in a molar ratio of acid to alkali of 1:1. The volatilising reactants were removed by placing in a slight air stream for approximately 15 hours. The HPC was then purified by the admixture of 200 ml of distilled water and subsequent dialysis (MWCO 1000 dialysis tubes, Serva) first with a continuous stream of water for 5 hours and then in 5 liters for 16 hours at 4° C. The purified samples were dried in evaporating dishes under reduced pressure at 70° C. for 20 hours. The HPC samples were then comminuted by grinding at low temperatures, before the MS values were determined by solid-state NMR. All stages of the process were subjected to gravimetric analysis and exhibited complete transformation of the material into the respective subsequent process stage. The results are given in the Table below.

Example 7

Cellulose samples were pretreated by incubation in water, buffer or puffer containing 6% (v/w) Denimax Ultra L® according to the description in Example 6. Before the chemical conversion, distilled water was added to the reaction mixtures in varying amounts. HPC was then prepared, purified and analysed according to Example 6. The results are shown in the following Table and in FIG. 7.

| Change on conditions | Buffer | 6% Denimax Ultra L® MS Values | 15% Denimax Ultra L® | Increase | Example |
|---|---|---|---|---|---|
| 1) Chemical conversion with shaking at 200 rpm<br>2) Water content 1.7 g/g of cellulose | 0.93 | — | 1.79 | 91% | 2 |
| 1) Chemical conversion with shaking at 200 rpm Optimum water content | 0.90 | 2.35 | — | 161% | 3 |

What is claimed is:

1. Process for the preparation of hydroxyalkylcellulose ethers from the reaction of alkene oxides and activated cellulose, characterised in that the cellulose is pretreated as follows:
   a) incubation in a buffer solution or water or a solvent/buffer or water mixture and endoglucanase,
   b) separation of the cellulose pretreated with endoglucanase from the buffer or water or solvent/buffer or water mixture,
   c) reaction of the activated cellulose to substituted cellulose derivatives by reaction with alkene oxides in the presence of catalytic alkali.

2. Process according to claim 1, characterized in that the endoglucanases are used from the group consisting of fungi, bacteria and plants.

3. Process according to claim 1, characterized in that the incubation is carried out at a temperature of from 0° C. to 100° C. for a period of from 0.1 to 24 hours.

4. Process according to claim 1, characterised in that the incubation is carried out in water or buffer or in a water/buffer or water mixture with a buffer concentration in the aqueous phase of from 0 to 1000 mM and a pH value of from 1 to 13.

5. Process according to claim 1, characterised in that the incubation is carried out with endoglucanase enzyme in a concentration of from 0.01 to 50% of the weight of the cellulose.

6. Process according to claim 1, characterised in that the incubation is carried out in the presence of a suitable concentration of biocides to prevent the growth of microorganisms and fungi.

7. The process of claim 2 wherein fungi are selected from the group consisting of *Trichoderma reesei* and *Humicola insolens*.

8. The process of claim 2 wherein bacteria are selected from the group consisting of Bacillus, Cellulomonas, Sprocytophaga, Cytophaga, Clostridium and Denimax Ultra L®.

9. The process of claim 3 wherein temperature is from 10° C. to 80° C.

10. The process of claim 3 wherein temperature is from 50° C. to 60° C.

11. The process of claim 3 wherein period is from 0.5 to 15 hours.

12. The process of claim 3 wherein period is from 2 to 5 hours.

13. The process of claim 4 wherein concentration is 10 to 100 mM.

14. The process of claim 4 wherein concentration is 50 mM.

15. The process of claim 4 wherein pH is 2 to 10.

16. The process of claim 4 wherein pH is from 5 to 7.5.

17. The process of claim 5 wherein concentration is 0.5 to 30%.

18. The process of claim 5 wherein concentration is 3 to 15%.

* * * * *